(12) United States Patent (10) Patent No.: US 8,656,919 B2
Bhat et al. (45) Date of Patent: Feb. 25, 2014

(54) SYSTEM FOR PREVENTION AND TREATMENT OF PRESSURE ULCERS

(75) Inventors: Nikhil Bhat, Fremont, CA (US); George Y. Choi, Atherton, CA (US)

(73) Assignee: PRS Medical Technologies, Inc., Atherton, CA (US)

( * ) Notice: Subject to any disclaimer, the term of this patent is extended or adjusted under 35 U.S.C. 154(b) by 23 days.

(21) Appl. No.: 13/407,628

(22) Filed: Feb. 28, 2012

(65) Prior Publication Data

US 2013/0019881 A1 Jan. 24, 2013

Related U.S. Application Data

(63) Continuation-in-part of application No. 13/189,320, filed on Jul. 22, 2011.

(51) Int. Cl.
*A61G 15/00* (2006.01)
*A61F 5/37* (2006.01)
*A61F 13/00* (2006.01)
*A61B 19/00* (2006.01)
*A61F 5/00* (2006.01)

(52) U.S. Cl.
USPC ........... 128/845; 128/846; 128/869; 128/888; 128/898; 602/5; 602/13; 602/19; 602/20

(58) Field of Classification Search
USPC .......... 128/846, 869, 888, 889; 602/5, 13, 19, 602/20
See application file for complete search history.

(56) References Cited

U.S. PATENT DOCUMENTS

| | | | |
|---|---|---|---|
| 3,748,669 A | 7/1973 | Warner | |
| 4,175,548 A | 11/1979 | Henry | |
| 4,483,030 A * | 11/1984 | Flick et al. | 5/691 |
| 4,534,078 A | 8/1985 | Viesturs et al. | |
| 4,559,933 A | 12/1985 | Batard et al. | |
| 4,617,690 A | 10/1986 | Grebe | |
| 4,622,957 A | 11/1986 | Curlee | |
| 4,682,588 A | 7/1987 | Curlee | |
| 4,726,624 A | 2/1988 | Jay | |
| 5,040,525 A | 8/1991 | Georgijevic | |
| 5,122,111 A | 6/1992 | Sebastian et al. | |
| 5,152,023 A | 10/1992 | Graebe | |
| 5,303,436 A | 4/1994 | Dinsmoor, III et al. | |
| 5,388,292 A | 2/1995 | Stinson et al. | |
| 5,421,874 A | 6/1995 | Pearce | |
| 5,489,259 A | 2/1996 | Jacobs et al. | |
| 5,671,552 A * | 9/1997 | Pettibone et al. | 36/27 |
| 5,794,289 A | 8/1998 | Wortman et al. | |
| 5,829,081 A | 11/1998 | Pearce | |

(Continued)

FOREIGN PATENT DOCUMENTS

WO WO 2007/047379 4/2007
WO WO 2013/016241 1/2013

*Primary Examiner* — Patricia Bianco
*Assistant Examiner* — Brandon L Jackson
(74) *Attorney, Agent, or Firm* — Levine Bagade Han LLP

(57) ABSTRACT

System for the prevention and treatment of pressure ulcers are described in which a portable support assembly may be worn by a bed-stricken individual around particular regions of the body where pressure ulcers tend to form. The portable support assembly may generally include one or more individual spring assemblies which are enclosed entirely within an inner fluid and/or outer fluid pad which extends over the entire assembly. Each of the spring assemblies may be secured to an outer shell which is relatively stiffer than the fluid layers.

21 Claims, 9 Drawing Sheets

(56) References Cited

U.S. PATENT DOCUMENTS

| | | | |
|---|---|---|---|
| 6,012,188 A | 1/2000 | Daniels et al. | |
| 6,020,055 A | 2/2000 | Pearce | |
| 6,026,527 A | 2/2000 | Pearce | |
| 6,065,166 A | 5/2000 | Sharrock et al. | |
| 6,197,099 B1 | 3/2001 | Pearce | |
| 6,560,803 B2 | 5/2003 | Zur | |
| 6,874,185 B1 | 4/2005 | Phillips et al. | |
| 6,896,662 B2 * | 5/2005 | Heffez | 602/19 |
| 7,060,213 B2 | 6/2006 | Pearce | |
| 7,063,677 B1 | 6/2006 | Daggett | |
| 7,141,032 B2 | 11/2006 | Flam et al. | |
| 7,216,388 B2 | 5/2007 | Bieganek et al. | |
| 7,254,852 B2 | 8/2007 | Martin | |
| 2003/0120191 A1 | 6/2003 | Clement | |
| 2006/0010607 A1 | 1/2006 | Schneider | |
| 2009/0070939 A1 | 3/2009 | Hann | |
| 2009/0194115 A1 | 8/2009 | Squitieri | |
| 2009/0254015 A1 | 10/2009 | Segal et al. | |
| 2010/0152821 A1 | 6/2010 | Rein et al. | |
| 2010/0229308 A1 * | 9/2010 | Pearce et al. | 5/655.5 |
| 2011/0099714 A1 * | 5/2011 | Svoboda | 5/499 |
| 2011/0126356 A1 * | 6/2011 | Steppat et al. | 5/727 |
| 2012/0311787 A1 | 12/2012 | Purdy et al. | |
| 2013/0019873 A1 | 1/2013 | Choi et al. | |
| 2013/0092175 A1 | 4/2013 | Bhat et al. | |
| 2013/0112213 A1 | 5/2013 | Bhat et al. | |
| 2013/0174855 A1 | 7/2013 | Choi et al. | |
| 2013/0174856 A1 | 7/2013 | Choi et al. | |
| 2013/0174859 A1 | 7/2013 | Bhat et al. | |
| 2013/0180530 A1 | 7/2013 | Choi et al. | |
| 2013/0180531 A1 | 7/2013 | Choi et al. | |

* cited by examiner

SYSTEM FOR PREVENTION AND TREATMENT OF PRESSURE ULCERS

FIELD OF THE INVENTION

This application is a continuation-in-part of U.S. application Ser. No. 13/189,320 filed Jul. 22, 2011, which is incorporated herein by reference in its entirety.

FIELD OF THE INVENTION

The present invention relates to devices and methods for preventing and treating pressure ulcers. More particularly, the present invention relates to devices and methods for preventing and treating pressure ulcers with cushioning devices which are portable and easily conformed to various regions of the patient's body by utilizing individual cushioning pods which are supported within an inner fluid pad as well as an outer fluid pad.

BACKGROUND OF THE INVENTION

Individuals who are forced to sit or lie down for extended periods of time typically experience tissue necrosis over localized regions of their body known as decubitus ulcers or pressure sores. These pressure ulcers generally occur at locations of the body where the bony prominence is high and the underlying skin breaks down when constant pressure is placed against the skin. Blood circulation is inhibited or prevented in these localized areas and can even occur when the patient has been lying against or upon cushioning devices. Examples of areas of the body where pressure sores typically occur include the sacrum, greater trochanter, ischial tuberosity, malleolus, heel, etc. When pressure ulcers form, they can lead to extensive stays in the hospital or even to amputation.

Conventional cushioning devices generally utilize flexible materials such as foam or springs which allow for the cushion to deform and conform to the patient's body. While the cushioning device attempts to redistribute the loading from localized regions of the patient's body to a larger area over the rest of the body, such devices typically bottom out such that the patient's body contacts the underlying platform and nonetheless localizes the pressure onto the body.

Other cushioning devices have utilized fluid-filled cushions which consist of large single bladders or compartmentalized fluid or gas-filled bladders which inhibit fluid contained within the bladders from flowing laterally. Such fluid-filled cushions attempt to hammock or suspend the patient's body while preventing the patient's body from bottoming out. However, such devices typically require a large area for placement beneath the patient or require specialized bedding.

Yet other cushioning devices utilize segmented bladders in an attempt to isolate individual bladders from one another. Yet such segmented cushions may fail to allow for the cushion to fully conform to the patient's body as fluid between each of the segmented cushions is prevented.

Accordingly, there exists a need for a cushioning device which may conform to regions of the patient's body to prevent decubitis ulcers in a manner which is more cost efficient, convenient, and effective.

BRIEF SUMMARY OF THE INVENTION

A portable support assembly may be worn by an individual who may be bed-stricken for an extended period of time to prevent the formation of pressure ulcers. Such a portable support assembly may be worn by the individual around particular regions of the body where pressure ulcers tend to form, e.g., sacrum, trochanter, ischium, as well as any other region of the body where support is desired. The portable support assembly may be formed into an elongated shape to be wrapped entirely around the patient's body, e.g., around the hips or lower back, or a portion of the body, e.g., around the ankles or feet. Alternatively, the support assembly may be placed upon a bed or platform (or directly integrated into the bed or platform) upon which the patient is resting.

The support assembly may be configured to be portable such that it may be worn directly over or upon the patient's body independently from the underlying bed or cushion. Accordingly, the patient may utilize the support assembly on any underlying bed or platform. Additionally, while the examples described illustrate portable support assemblies, the support assembly may be integrated into a bed, underlying cushion, and/or mattress pad if so desired and as previously described.

Generally, the support assembly may comprise one or more pods positioned adjacent to one another, an inner pad enclosing the one or more pods such that compression of the pods is controlled by the inner pad, an outer pad enclosing the inner pad, and an outer shell attached to the outer pad, wherein the outer shell is sufficiently flexible to be worn upon a portion of a subject's body.

In use, the support assembly may support the desired region of the body by securing a portable support assembly directly to the region of the body to be supported, controlling displacement of one or more pods positioned along the support assembly beneath the region via an inner pad enclosing the one or more pods, and redistributing a pressure load from the one or more pods and inner pad to an outer pad positioned along the support assembly and enclosing the inner pad, wherein the redistributed pressure load is exerted upon the body surrounding the supported region.

One variation of the portable support assembly may generally define a securement area for placement against the region of the body requiring support such as the sacrum. The securement area may generally comprise a central portion with a first conformable portion and/or second conformable portion extending from either side of the central portion. The first and/or second conformable portions may be flexible enough to allow for the portions to be wrapped around or about at least a portion of the patient's body such that the assembly may remain secured to the body even when the patient moves about thereby maintaining the central portion against the supported region of the body.

The central portion may provide the greatest amount of localized support to the patient body by utilizing several fluid layers which are contained one within another to receive the localized loading from the protuberance from the patient's body and distribute the localized load onto the surrounding areas and to further control displacement or inhibit or prevent the bottoming out of the fluid layers. The central portion may thus contain one or more fluid filled individual pods which may be enclosed entirely within an inner fluid pad which envelopes the one or more pods within a secondary layer of fluid. The inner fluid pad may be localized along the central portion. Both the one or more pods and inner fluid pad are then enclosed entirely by a tertiary layer of fluid within an outer fluid pad which may extend over the entire assembly. Each of the fluid layers may be secured to an outer shell which is relatively stiffer than the fluid layers and may restrict or limit the expansion or movement of the fluid pods and/or fluid pads. While the assembly is adjustable to fit a particular patient, the outer pad, in particular, may optionally be filled with the fluid to a variable amount to further ensure that the assembly may be fitted or conformed to the anatomy of a particular patient.

Each of the one or more pods may be separated from one another such that no fluid communication occurs between the pods and/or with the inner pad. Similarly, the inner pad may be separate from the outer pad such that no fluid communication occurs between the two. In other variations, some fluid communication may occur between the inner pad and outer pad so long as the inner pad constrains and prevents the over-compression of the one or more pods to control their displacement and inhibit their bottoming out.

Each of the pods and/or fluid pads may be filled with an incompressible fluid such as water, viscous oil, or some other biocompatible fluid. Yet in other variations, the pods and/or fluid pads may be filled alternatively with a gas such as air, nitrogen, etc. In yet additional variations, the one or more pods and/or fluid pads may be filled with either a fluid or gas or a combination of both depending upon the desired degree of cushioning and force distribution.

The one or more fluid pods may each occupy an envelope of, e.g., 1 cm×1 cm×0.5 cm to about 3 cm×3 cm×3 cm, in an uncompressed state and they may be formed into various shapes, e.g., spherical, cylindrical, cubical, etc. Moreover, each of the pods may be formed from various materials such as polyurethane, silicone, vinyl, nylon, polyethylene vinyl acetate (PEVA), etc. having a thickness ranging from, e.g., 0.1 mm to 5 mm. Although the figure illustrates four pods, the number of pods contained within the inner pad may range anywhere from, e.g., 1 to 30 or more, arranged either uniformly or arbitrarily within the inner pad. Additionally, while the pods may be unconstrained within the inner pad such that they freely move relative to one another, the pods may be secured within the inner pad either to one another or to the inner pad itself such that their relative movement is constrained.

In yet other variations, rather than utilizing pods having a fluid contained within, one or more spring assemblies may be used to provide the cushioning support. These spring assemblies may utilize various spring types such as leaf or compression springs or various other types of biasing mechanisms.

In either case, the pods may transfer localized loads from the patient received by a few pods either to adjacent pods through the compression and transfer of pressure to adjacent contacting pods or through transmission via the fluid in the inner pad and/or outer pad. The amount of compression of the pods themselves may be controlled by the inner pad which envelopes the pods within a pad localized over the central portion. The inner pad may function as a hammocking layer to constrain the amount of displacement experienced by the individual pods but because the inner pad itself may be fluid filled, the inner pad may further provide support to the patient's body while also restricting compression of the pods. The amount of compression experienced by the individual pods may thus be controlled by the inner pad to range anywhere from, e.g., 0% to 90% (or 10% to 90%), of the uncompressed height of the pods.

The inner pad may be sized into various configurations depending upon, e.g., the number of pods or the area of the body to be supported. Moreover, the inner pad may also be made from the same or similar material as the pods, e.g., polyurethane, silicone, vinyl, nylon, polyethylene vinyl acetate (PEVA), etc. While the inner pad may be filled with a fluid (or gas or combination of both), as described above, the inner pad may alternatively be devoid of fluid and instead be used to constrain the expansion of the individual pods. Thus, inner pad may be optionally vented to allow for any trapped air to vent from between the pods when the pods undergo compression.

While the one or more pods and inner pad may be concentrated particularly around the region of the body to be supported, an additional outer pad may enclose and surround the inner pad which further encloses the one or more pods. The outer pad may be similarly filled with a fluid or gas (or combination of both), as described above, and may be enclosed by a layer of material either the same or similar to the material of the inner pad and/or pods and further have a uniform or variable thickness ranging from, e.g., 0.5 mm to 4 cm. The outer pad may further constrict the compression of the inner pad which in turn constricts the compression of the one or more pods while additionally providing cushioning support to the surrounding tissue or body structures. Moreover, the outer pad may further extend over the length of the entire assembly to provide cushioning support to the region of the body upon which the assembly is secured.

Further supporting the assembly is the outer shell which may function as a restricting support to control displacement and inhibit the further compression of the outer pad to prevent the patient's body from bottoming out. The outer shell may be formed on a single side of the assembly such that when the assembly is worn by the patient, the outer shell may be positioned away from the skin of the patient such that the outer pad remains in contact with the patient. The outer shell may be accordingly made to be relatively stiffer than the outer pad yet still be flexible enough for conforming over or around the patient's body. Accordingly, the outer shell may be made from materials including plastics such as polypropylene, ABS, PVC, polyethylene, nylon, acrylic, polycarbonate, etc. The outer shell may also be fabricated from other materials such as polymers, carbon fiber, light weight metals, elastomeric materials, rubbers, etc. Depending upon the material used, the outside shell can have a thickness ranging from, e.g., 1 mm to 3 cm.

When the patient wears the support assembly, the one or more fluid filled pods may thus support the body portion (such as the sacrum or trochanter) and due to the weight of the patient, the one or more pods may compress against one another by a limited amount. However, the one or more pods may be inhibited from bottoming out due to the surrounding hammocking inner pad. The pressure on the body portion may thus be reduced and distributed/transferred to the surrounding fluid present in the inner pad. Moreover, the presence of the surrounding outer pad may further transmit and redistribute the induced pressure upwards towards and against the surrounding body portions, such as the thigh area. This decrease in pressure can lead to a reduction in pressure against the localized body region to a value of less than or approximately 4.3 kPa and hence prevent tissue necrosis and reduce the occurrence of pressure ulcers.

In yet another variation, an assembly may further incorporate additional localized support regions along different portions of the assembly. Other variations of the assembly may incorporate baffles and other mechanisms to optionally create interconnected fluid regions. These regions may allow for reducing the amount of fluid in the entire system and prevent the fluid from pooling in one area.

In yet another variation, open cell foam may be placed between the individual inner and outer fluid layers. This foam layer may be saturated with fluid and allow for the transfer of fluid pressure between the different fluid layers.

Additional variations may incorporate a breathable layer covering at least a portion of the outer pad. The layer may be porous and can be made from materials such as cotton, etc., such that air may circulate through the pores or openings.

In yet other variations, one or more vibrating elements may be attached or integrated into the assembly, e.g., along the outer layer of the outer pad. These vibrating elements may vibrate to impart micro or macro vibrations directly against the contacted skin surface to relieve pressure over the contact area or into the fluid pad itself to indirectly vibrate against the skin surface. The vibrating elements may generate microvibrations on the order of about, e.g., 10 to 500 microns, in amplitude with a frequency ranging from about, e.g., 10 Hz to 300 Hz. These vibrations may allow for increased blood circulation and may also help decrease the incidence of pressure ulcers. Moreover, the vibrating elements may be comprised of piezoelectric, nitinol, or any other actuator driven elements.

In yet other variations, any of the embodiments described herein may incorporate various temperature control mechanisms. These may include one or more regions within the support pad assemblies which may be cooled and/or heated to prevent and/or treat pressure ulcers.

With any of the variations described herein, different features and aspects from each of the variations may be combined with one another in various combinations.

DETAILED DESCRIPTION OF THE INVENTION

Figure 1A:
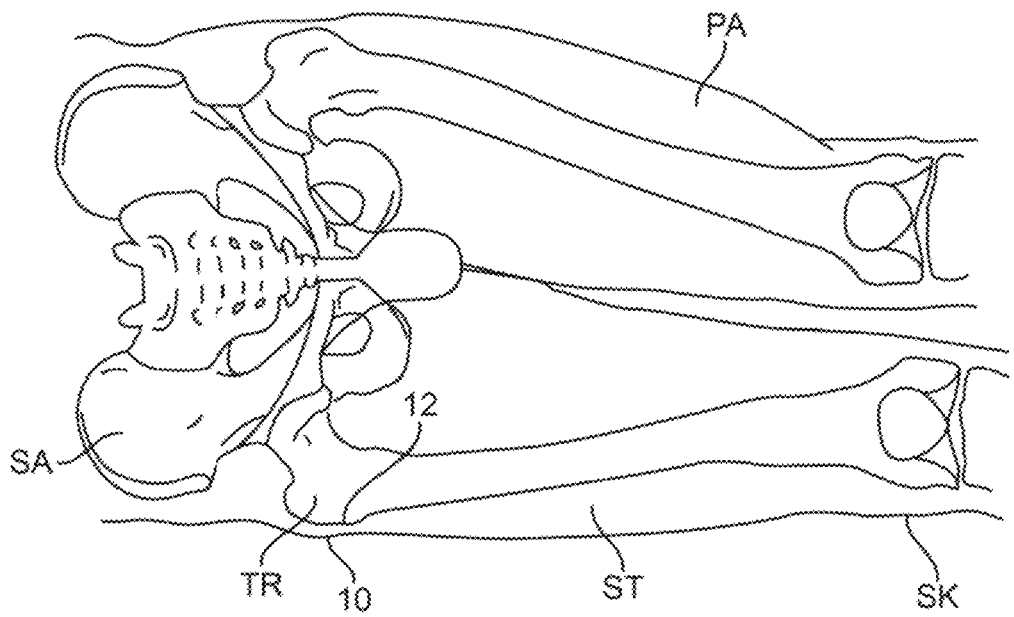
FIG. 1A shows a portion of a patient's body and the resultant induced pressure imparted on portions of the body such as the trochanter.

Generally, in a healthy individual, the presence of muscle mass and soft tissue ST usually functions to distribute and relieve pressure from bony protuberances of the body contacted against the underlying surface. However, when a patient PA is forced to lie on one portion of their body for extended periods of time, areas such as the sacrum SA or trochanter TR may compress a region of the skin SK and tissue 12 between the protuberance and a contact region 10 formed against the underlying surface, as shown in FIG. 1A.

Typical pressures generated in the hip area for healthy individuals lying against a surface may range around 4 kPa. However, for older and/or diseased individuals, the contact pressures between regions of bony prominence and the skin is generally higher due to various factors such as muscle atrophy. For instance, increased pressures were found to range around 7.3 kPa. Blood circulation become restricted and tissue necrosis typically begins when pressures range above 4.3 kPa leading to the development of pressure ulcers.

Figure 1B:
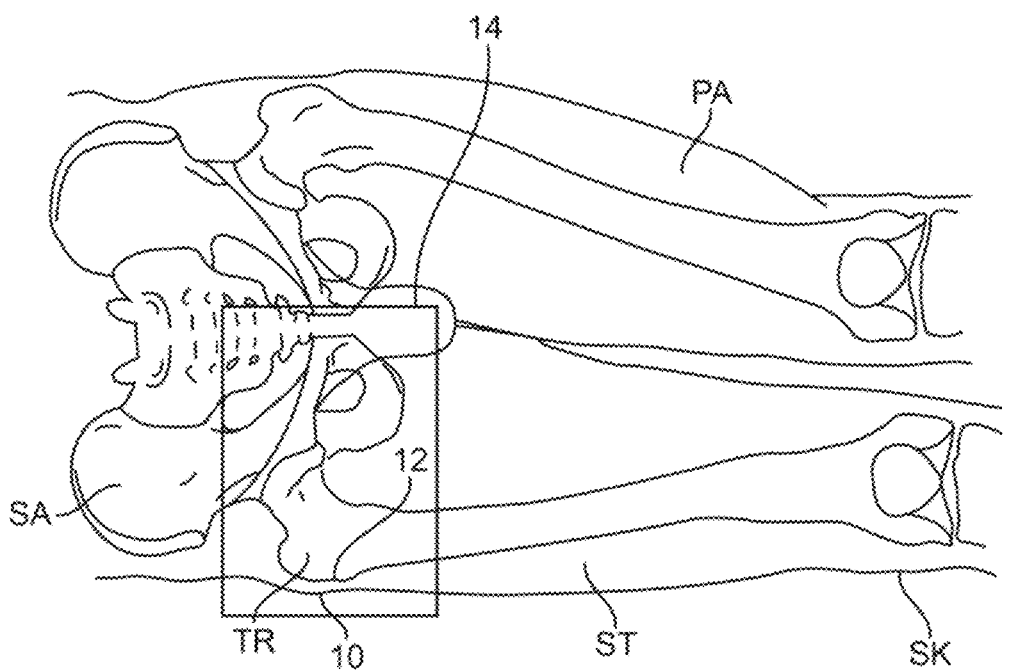
FIG. 1B shows a portion of the patient's body with a portable support assembly worn upon the body, e.g., around the hips, to alleviate pressure.

Generally, a portable support assembly 14 may be worn by an individual who may be bed-stricken for an extended period of time to prevent the formation of pressure ulcers. Such a portable support assembly 14 may be worn by the individual around particular regions of the body where pressure ulcers tend to form, e.g., sacrum SA, trochanter TR, ischium, as well as any other region of the body where support is desired. The portable support assembly 14 may be formed into an elongated shape to be wrapped entirely around the patient's body, e.g., around the hips or lower back, or a portion of the body, e.g., around the ankles or feet. Thus, although the example shown in FIG. 1B illustrates the assembly 14 placed around the trochanter TR or sacrum SA, other embodiments may include various shapes of the assembly 14 which may be sized for particular body regions and are intended to be within the scope of this disclosure.

Moreover, the support assembly 14 is configured to be portable such that it may be worn directly over or upon the patient's body independently from the underlying bed or cushion. Accordingly, the patient may utilize the support assembly 14 on any underlying bed or platform. Additionally, while the examples described illustrate portable support assemblies, the support assembly may be integrated into a bed, underlying cushion, and/or mattress pad if so desired.

Figure 2:
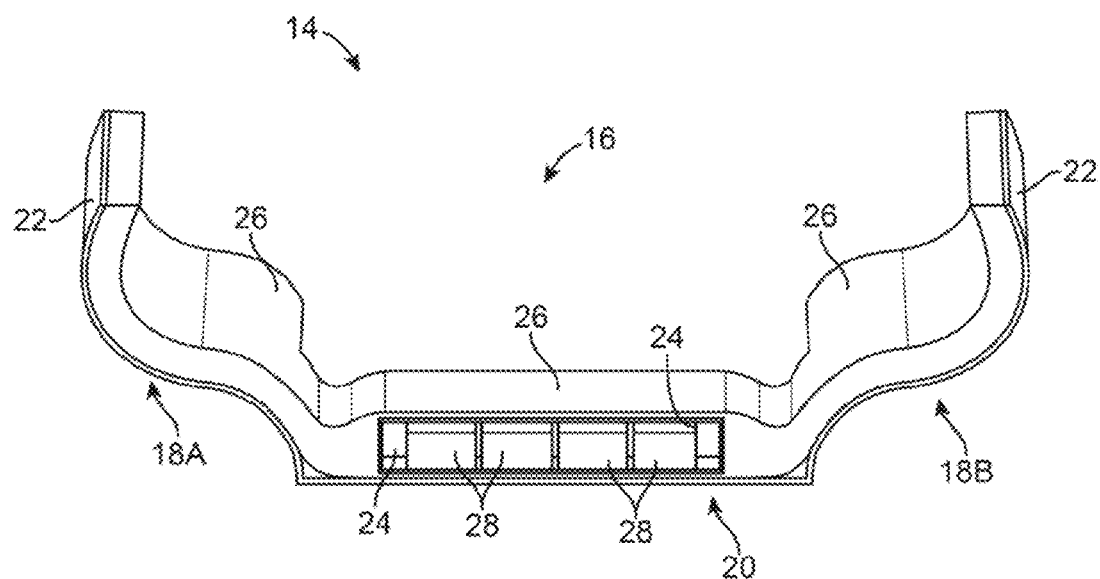
FIG. 2 shows a cross-sectional end view of one variation of a portable support assembly illustrating the various layered fluid pads contained within.

One variation of the portable support assembly 14 is illustrated in the cross-sectional view of FIG. 2, which illustrates a wearable hip-support system. In this variation, the support assembly 14 may generally define a securement area 16 for placement against the region of the body requiring support such as the sacrum SA. The securement area 16 may generally comprise a central portion 20 with first conformable portion 18A and/or second conformable portion 18B extending from either side of the central portion 20. The first and/or second conformable portions 18A, 18B may be flexible enough to allow for the portions 18A, 18B to be wrapped around or about at least a portion of the patient's body such that the assembly 14 may remain secured to the body even when the patient moves about thereby maintaining the central portion 20 against the supported region of the body.

The central portion 20 may provide the greatest amount of localized support to the patient body by utilizing several fluid layers which are contained one within another to receive the localized loading from the protuberance from the patient's body and distribute the localized load onto the surrounding areas and to further control their displacement and inhibit or prevent the bottoming out of the fluid layers. The central portion 20 may thus contain one or more fluid filled individual pods 28 which may be enclosed entirely within an inner pad 24 which envelopes the one or more pods 28 within a secondary layer of fluid. The inner pad 24 may be localized along the central portion 20. The inner pad 24 may be filled with a fluid (or gas) or optionally be devoid of any fluid, as described in further detail below. Both the one or more pods 28 and inner pad 24 are then enclosed entirely by a tertiary layer of fluid within an outer pad 26 which may extend over the entire assembly 14. Each of the fluid layers may be secured to an outer shell 22 which is relatively stiffer than the fluid layers and may restrict or limit the expansion or movement of the fluid pods 28 and/or pads 24, 26. While the assembly 14 is adjustable to fit a particular patient, the outer pad 26, in particular, may optionally be filled with the fluid to a variable amount to further ensure that the assembly 14 may be fitted or conformed to the anatomy of a particular patient.

Each of the one or more pods 28 may be separated from one another such that no fluid communication occurs between the pods 28 and/or with the inner pad 24. Similarly, the inner pad 24 may be separate from the outer pad 26 such that no fluid communication occurs between the two. In other variations, some fluid communication may occur between the inner pad 24 and outer pad 26 so long as the inner pad 24 constrains and prevents the over-compression of the one or more pods 28 to control their displacement and inhibit their bottoming out.

Each of the pods 28 and/or fluid pads 24, 26 may be filled with an incompressible fluid such as water, salt solution, viscous oil, or some other biocompatible fluid. Yet in other variations, the pods 28 and/or fluid pads 24, 26 may be filled alternatively with a gas such as air, nitrogen, etc. In yet additional variations, the one or more pods 28 and/or fluid pads 24, 26 may be filled with either a fluid or gas or a combination of both depending upon the desired degree of cushioning and force distribution.

The one or more fluid pods 28 may each occupy an envelope of, e.g., 1 cm×1 cm×0.5 cm to about 3 cm×3 cm×3 cm, in an uncompressed state and they may be formed into various shapes, e.g., spherical, cylindrical, cubical, etc. Moreover, each of the pods may be formed from various materials such as polyurethane, silicone, vinyl, nylon, polyethylene vinyl acetate (PEVA), etc. having a thickness ranging from, e.g., 0.1 mm to 5 mm. Although the figure illustrates four pods 28, the number of pods 28 contained within the inner pad 24 may range anywhere from, e.g., 1 to 30 or more, arranged either uniformly or arbitrarily within the inner pad 24. Additionally, while the pods 28 may be unconstrained within the inner pad 24 such that they freely move relative to one another, the pods 28 may be secured within the inner pad 24 either to one another or to the inner pad 24 itself such that their relative movement is constrained.

In either case, the pods 28 may transfer localized loads from the patient received by a few pods 28 either to adjacent pods through the compression and transfer of pressure to adjacent contacting pods or through transmission via the fluid in the inner pad 24 and/or outer pad 26. The amount of compression of the pods 28 themselves may be controlled by the inner pad 24 which envelopes the pods 28 within a pad localized over the central portion 20. The inner pad 24 may function as a hammocking layer to constrain the amount of displacement experienced by the individual pods 28 but because the inner pad 24 itself may be fluid filled, the inner pad 24 may further provide support to the patient's body while also restricting compression of the pods 28. The amount of compression experienced by the individual pods 28 may thus be controlled by the inner pad 24 to range anywhere from, e.g., 0% to 90% (or 10% to 90%), of the uncompressed height of the pods 28. For example, for a pod 28 having an uncompressed height of 3 cm, the compression of the pod 28 may range anywhere from, e.g., 0 cm to 2.7 cm.

The inner pad 24 may be sized into various configurations depending upon, e.g., the number of pods 28 or the area of the body to be supported. Moreover, the inner pad 24 may also be made from the same or similar material as the pods 28, e.g., polyurethane, silicone, vinyl, nylon, polyethylene vinyl acetate (PEVA), etc. While the inner pad 24 may be filled with a fluid (or gas or combination of both), as described above, the inner pad 24 may alternatively be devoid of fluid and instead be used to constrain the expansion of the individual pods 28. Thus, inner pad 24 may be optionally vented to allow for any trapped air to vent from between the pods 28 when the pods 28 undergo compression.

While the one or more pods 28 and inner pad 24 may be concentrated particularly around the region of the body to be supported, an additional outer pad 26 may enclose and surround the inner pad 24 which further encloses the one or more pods 28. The outer pad 26 may be similarly filled with a fluid or gas (or combination of both), as described above, and may be enclosed by a layer of material either the same or similar to the material of the inner pad 24 and/or pods 28 and further have a uniform or variable thickness ranging from, e.g., 0.5 mm to 4 cm. The outer pad 26 may further constrict the compression of the inner pad 24 which in turn constricts the compression of the one or more pods 28 while additionally providing cushioning support to the surrounding tissue or body structures. Moreover, the outer pad 26 may further extend over the length of the entire assembly 14 to provide cushioning support to the region of the body upon which the assembly 14 is secured.

Additionally, while the outer pad 26 may have a thickness ranging anywhere from, e.g., 5 mm to 2 cm or more (such as in areas in contact against the sacrum), the inner pad 24, outer pad 26, and/or pods 28 may be filled with a fluid having a density which is relatively higher than the density of a body. For example, the density of the human body is about 1.01 g/cm$^2$ and a salt solution filled within any of the pads 24, 26 and/or pods 28 can have density of, e.g., 1.03 to 1.1 g/cm$^2$. By using a highly saturated salt solution used as the fluid, a further cushioning effect may be achieved for providing comfort to the patient when the assembly is in use.

Further supporting the assembly is the outer shell 22 which may function as a restricting support to control displacement and inhibit the further compression of the outer pad 26 to prevent the patient's body from bottoming out. The outer shell 22 may be formed on a single side of the assembly 14 such that when the assembly 14 is worn by the patient, the outer shell 22 may be positioned away from the skin of the patient such that the outer pad 26 remains in contact with the patient. The outer shell 22 may be accordingly made to be relatively stiffer than the outer pad 26 yet still be flexible enough for conforming over or around the patient's body. Accordingly, the outer shell 22 may be made from materials including plastics such as polypropylene, ABS, PVC, polyethylene, nylon, acrylic, polycarbonate, etc. The outer shell 22 may also be fabricated from other materials such as polymers, carbon fiber, light weight metals etc. Depending upon the material used, the outside shell 22 can have a thickness ranging from, e.g., 1 mm to 3 cm.

When the patient wears the support assembly, the one or more fluid filled pods 28 may thus support the body portion (such as the sacrum SA or trochanter TR) and due to the weight of the patient, the one or more pods 28 may compress against one another by a limited amount. However, the one or more pods 28 may be inhibited from bottoming out due to the surrounding hammocking inner pad 24. The pressure on the body portion may thus be reduced and distributed/transferred to the surrounding fluid present in the inner pad 24. Moreover, the presence of the surrounding outer pad 26 may further transmit and redistribute the induced pressure upwards towards and against the surrounding body portions, such as the thigh area. This decrease in pressure can lead to a reduction in pressure against the localized body region to a value of less than or approximately 4.3 kPa and hence prevent tissue necrosis and reduce the occurrence of pressure ulcers.

In another variation, the one or more pods 28 may be connected directly to the outer shell 22 and contained by the hammocking inner pad layer 24 which prevents the pods 28 from bottoming out, as described above. The outer fluid pad 26 may be laid atop the one or more pods 28 and hammocking inner layer 24. Alternatively, the one or more pods 28 (contained within the hammocking inner layer 24) may come into direct contact against the patient and the outer fluid pad 26 may instead be attached directly to the outer shell 22.

Figure 3:
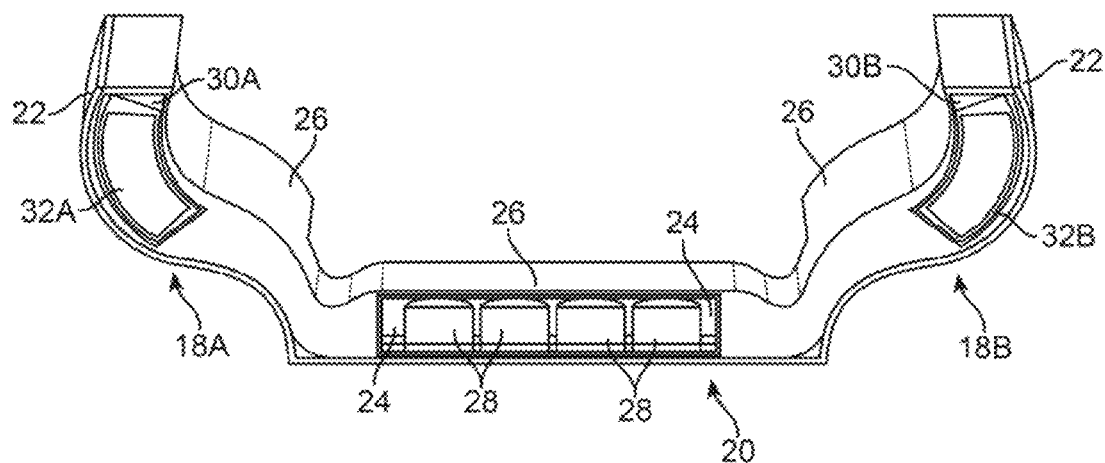
FIG. 3 shows a cross-sectional end view of another variation of the support assembly illustrating additional fluid pads contained within.

In yet another variation, FIG. 3 shows a cross-sectional view of an assembly which is similarly constructed to the variation of FIG. 2 but which may further incorporate additional localized support regions. For instance, in the variation shown, a first fluid inner pad 30A having one or more pods 32A contained within may be integrated along the first conformable portion 18A extending from the central portion 20. Similarly, a second fluid inner pad 30B having one or more pods 32B contained within may be integrated along the second conformable portion 18B extending from the opposite side of the central portion 20. In this variation, the conformable portions 18A, 18B may be wrapped or secured against the hips of the patient such that the corresponding inner pads 30A, 30B are positioned over either or both trochanters TR of the patient while the central portion 20 is positioned over the sacrum SA to provide support around the entire hip and lower back regions of the patient. As described herein, the number and size of the pods 32A, 32B may be varied.

Figure 4A:
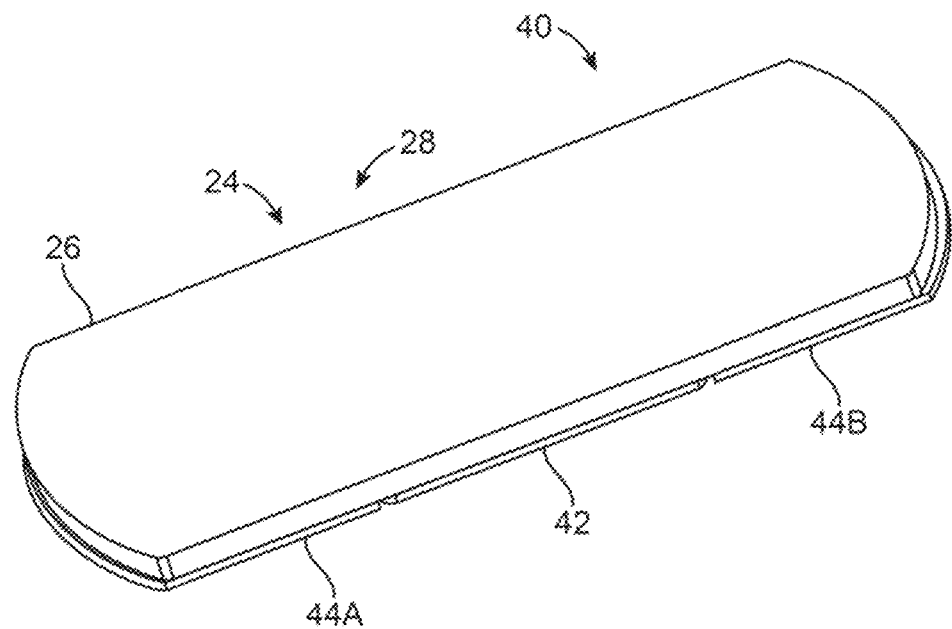
FIGS. 4A and 4B show perspective views of another variation of the support assembly which may be layered upon a hinged platform.
Figure 4B:
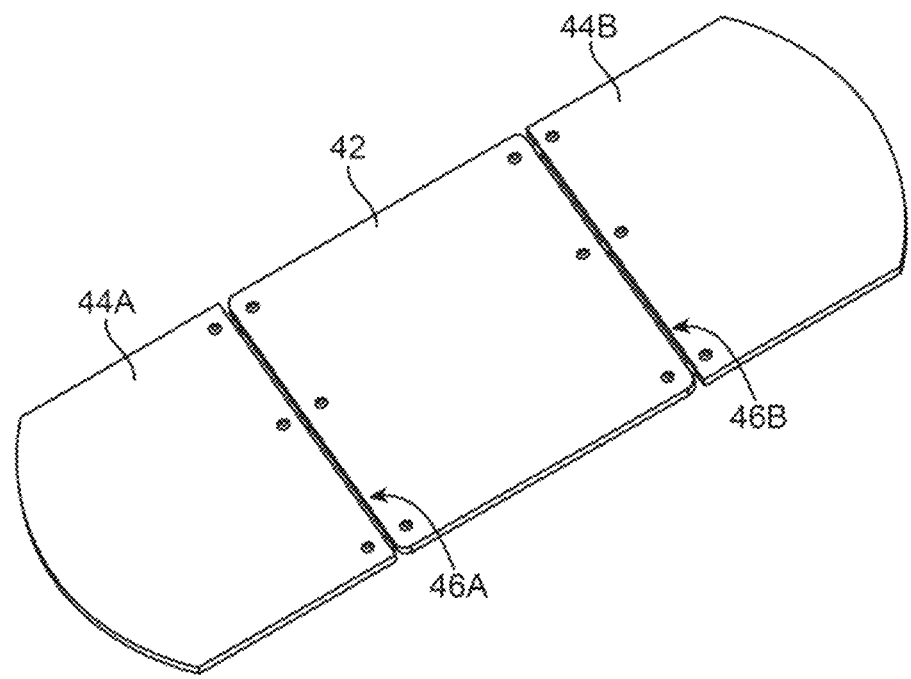

While the support assembly 14 may be sized in various configurations depending upon the region of the body to which the assembly is to be positioned, another example of an assembly configuration is shown in the perspective views of FIGS. 4A and 4B. In this example, the support system may be configured as a hinged fluid pad assembly 40 having a central portion 42 and a first foldable portion 44A and a second foldable portion 44B extending from either side of the central portion 42. The outer shell of the foldable portions 44A, 44B may be coupled via corresponding first hinged region 46A and second hinged region 46B such that the assembly 40 may be laid flat upon a bed or platform. The inner fluid pad 24 and one or more pods 28 may be positioned upon the central portion 42 and/or optionally along the first and/or second foldable portions 44A, 44B as well while the outer pad 26 may extend continuously along the length of the entire assembly 40. In use, the assembly 40 may be laid flat and folded over upon or against the patient's body and secured accordingly.

Other variations of the assembly may incorporate baffles and other mechanisms to optionally create interconnected fluid regions. These regions may allow for reducing the amount of fluid in the entire system and prevent the fluid from pooling in one area.

In yet another variation, open cell foam may be placed between the individual inner and outer fluid layers. This foam layer may be saturated with fluid and allow for the transfer of fluid pressure between the different fluid layers.

Figure 5:
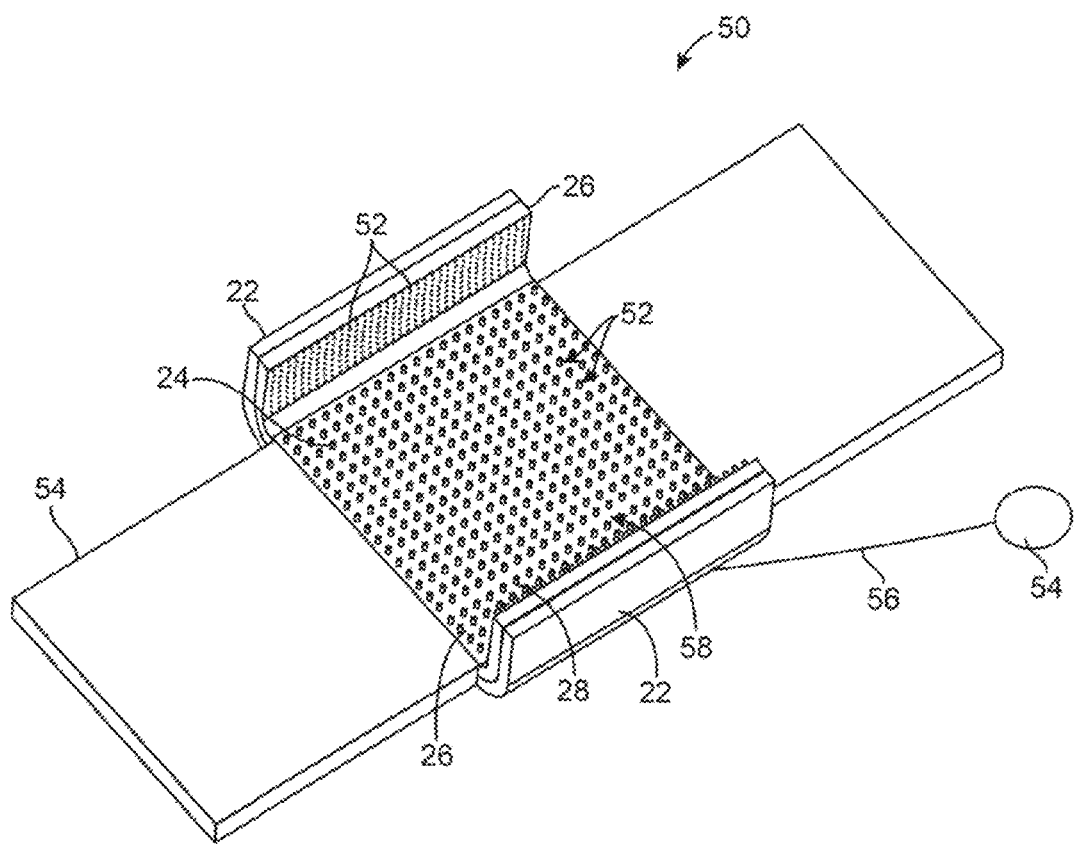
FIG. 5 shows a perspective view of yet another variation of the support assembly incorporating features such as a cooling mechanism and/or a plurality of vibrating elements.

FIG. 5 shows a perspective view of yet another variation in which the support assembly 50 may incorporate a breathable layer covering at least a portion of the outer pad 26. The layer may be porous and can be made from materials such as cotton, etc., such that air may circulate through the pores or openings 52. A pump 54 coupled via a fluid line 56 may be optionally attached to the assembly 50 to pump air through the pores or openings 52.

In yet other variations, one or more vibrating elements 58 may be attached or integrated into the assembly 50, e.g., along the outer layer of the outer pad 26. These vibrating elements 58 may vibrate to impart micro or macro vibrations directly against the contacted skin surface to relieve pressure over the contact area or into the fluid pad itself to indirectly vibrate against the skin surface. The vibrating elements 58 may generate micro-vibrations on the order of about, e.g., 10 to 500 microns, in amplitude with a frequency ranging from about, e.g., 10 Hz to 300 Hz. These vibrations may allow for increased blood circulation and may also help decrease the incidence of pressure ulcers. Moreover, the vibrating elements 58 may be comprised of piezoelectric, nitinol, or any other actuator driven elements.

In other variations, the assembly 50 may be integrated with an optional mattress topper 54 to provide stability to the assembly 50 when positioned against the patient.

Figure 6A:
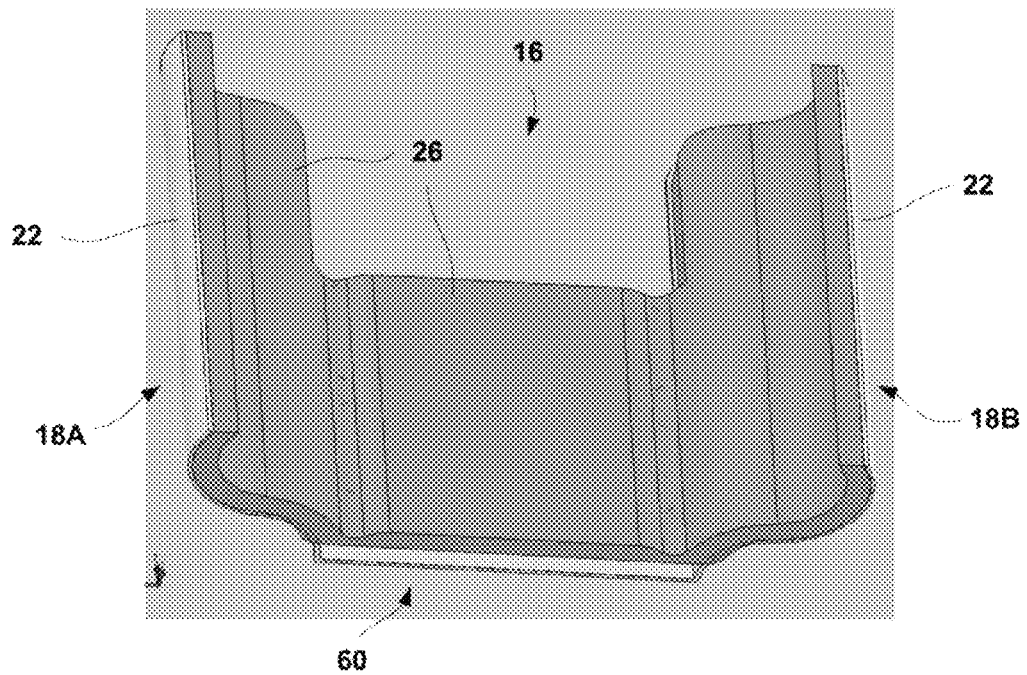
FIGS. 6A and 6B show perspective and side views of another variation of the support assembly which utilizes one or more spring assemblies in combination with the inner and/or outer pad.
Figure 6B:
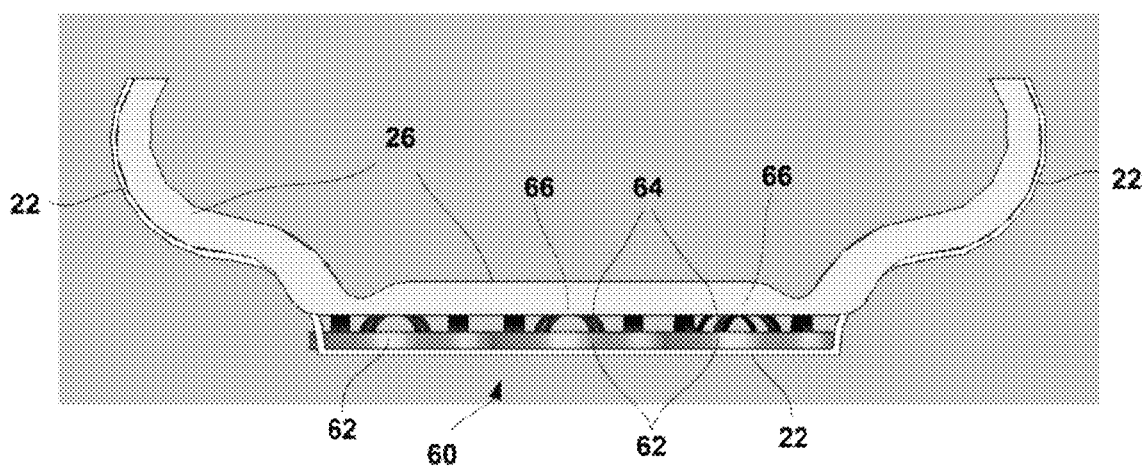

In yet another variation, the support assembly may utilize one or more spring assemblies in combination with the inner pad 24 and/or outer pad 26 rather than using the one or more pods 28. An example is shown in the perspective view of FIG. 6A which shows a variation of the assembly with outer pad 26 positioned atop one or more spring assemblies 60 rather than one or more pods. FIG. 6B shows a partial cross-sectional side view of one or more spring assemblies 60 secured upon the outer shell 22 and the outer pad 26 positioned atop the spring assemblies 60. The number of individual compression assemblies 60 in the array can vary, e.g., from 1 to 25 or more depending upon the desired treatment area. Moreover, each of the individual spring assemblies 60 is designed to be non-bottoming and further designed to reduce the pressure to less than or equal to, e.g., 32 mm of Hg, when a person uses the system.

One variation of a spring assembly may have an individual base 62 for securement to the outer shell 22 and a corresponding top layer 66 for contacting against the outer pad 26 and/or directly against the patient body. Between the top layer 66 and base 62 are one or more biasing members 64, e.g., spring elements. An example is shown in the perspective view of FIG. 7 which illustrates the top layer 66 and base 62 formed in a circular configuration although they may be formed in any number of shapes which are suitable for placement between the shell 22 and outer 26. The variation of biasing members 64 shown may comprise superelastic shape memory alloys such as heat-formed Nitinol formed, e.g., into flattened strips of material which are configured into leaf or compression springs, as shown. When a force is applied to the top layer 66, such as by the patient body, the biasing members 64 compress and their height decreases in response to the application of the force causing the top layer 66 to move towards the base 62.

Figure 7:
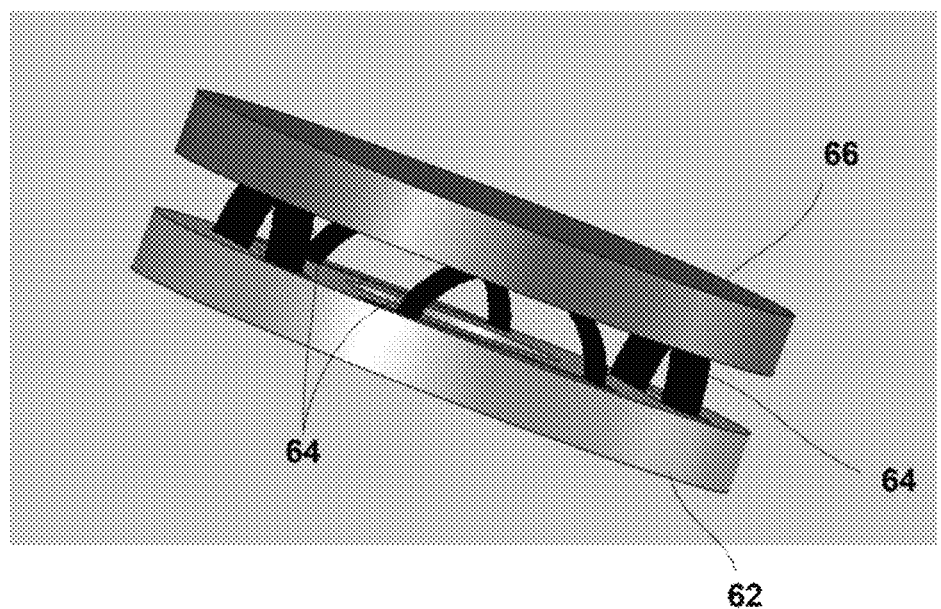
FIG. 7 shows a perspective view of one variation of a spring assembly.

The spring assembly shown in FIG. 7 is illustrated as having four biasing members 64 but the assembly can have one, two, three, or more biasing members 64. The biasing members 64 can also be made from other materials such as stainless steels, plastics, elastomers, and other suitable materials.

Figure 8:
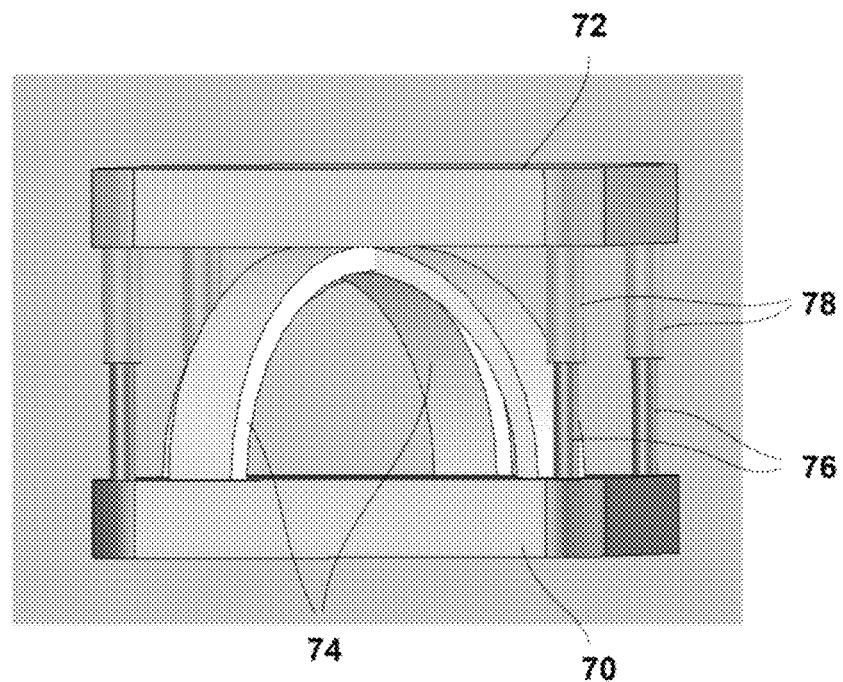
FIG. 8 shows a perspective view of another variation of a spring assembly.

FIG. 8 shows an alternative variation of a spring assembly having a base 70 and a top layer 72 with the biasing members 74 as previously described. The assembly may further have one or more post members 76 extending from the base 70 for translational engagement with one or more corresponding guide members 78 which may be aligned to receive the post members 76. The post members 76 may prevent the top layer 72 from rotating out of alignment with respect to base 70 during use. Moreover, the biasing members 74 may be designed to be a multiple prong anchor or flower design although any of the spring designs described herein may be used.

The individual spring assembly can have a surface area, e.g., from 0.5 to 1.0 cm$^2$ or even up to 200 cm$^2$, and an uncompressed height ranging from, e.g., 1 cm to 3 cm. The biasing members 64 can also vary from having a constant force to having compression systems with a single spring constant or multiple spring constants.

Moreover, various other biasing elements such as extension springs, leaf springs, torsion springs, or any formed or shaped design which can accomplish similar functions may be used. Aside from the design, the different kinds of springs and compression pods may be designed to have spring constants either independently or on a system level such that the displacement or travel to support the patient does not result in pressures greater than, e.g., 4.3 kPA or similar pressures, which can cause tissue necrosis and lead to formation of pressure ulcers.

Figure 9A:
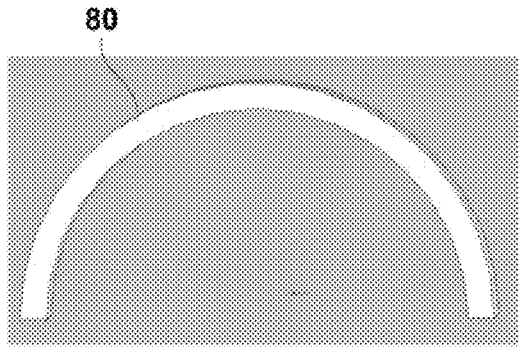
FIGS. 9A to 9D show various spring designs which may be used with any of the spring assemblies.
Figure 9B:
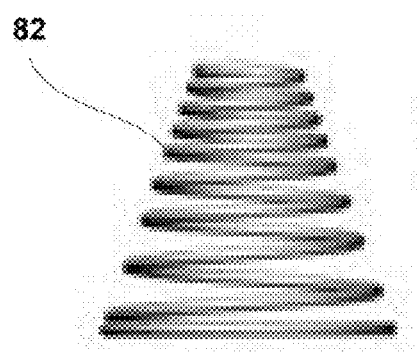
Figure 9C:
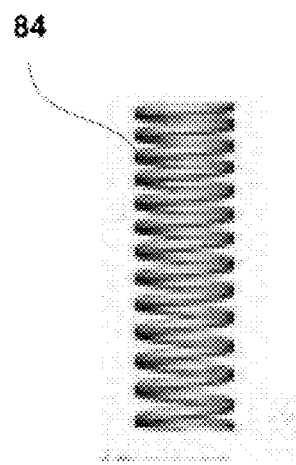
Figure 9D:
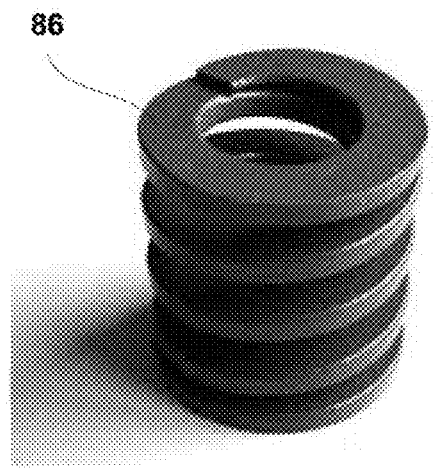

Other examples of various spring designs which may be used with any of the assemblies described herein are shown in FIGS. 9A to 9D. For instance, FIG. 9A shows a side view of a leaf spring 80 while FIGS. 9B and 9C show side views of a conical spring 82 and a cylindrical spring 84, respectively, which may be used as well. FIG. 9D shows a perspective view of an elastomeric spring 86 which may also be used, if so desired.

Experiment

Tests using exemplary embodiments of the support assembly described herein have been conducted utilizing an array of individual fluid pods enclosed within an inner enveloping pad. This assembly was then enveloped within an outer fluid pad where both the fluid pods and outer pads were filled with water. The assembly was positioned near a simulated sacrum region and a similar arrangement was positioned near a simulated trocanter region.

An artificial male hip model was used to which a 0 to 20 lb FLEXIFORCE® (Tekscan, Inc., MA) sensor was attached to the sacrum region of the hip model. The FLEXIFORCE® sensor was used to sense contact force/pressure and an 8 lb load (ball) was used as the simulated load of a patient.

A first test had the hip model placed on a simulated mattress having a foam pillow with a thickness of about 1 cm. The hip model was then loaded three times with the 8 lb load and a corresponding force reading was recorded. A second test was then conducted where the hip model was placed on the support assembly pad and was then loaded with the 8 lb load. The hip model was then loaded again three times with the 8 lb load and a corresponding force reading was recorded. The tabulated results are shown in the following table:

TABLE 1

Force measurements results from simulated loading.

| Test No | Force in N (simulated mattress) | Force in N (support assembly pad) | Force/Pressure (decrease by support assembly pad) |
|---|---|---|---|
| 1 | 7.70 | 4.29 | 44% |
| 2 | 6.33 | 3.42 | 46% |
| 3 | 5.65 | 3.42 | 39% |

Accordingly, use of the support assembly pad yielded an average reduction of 43% in measured pressure as experienced by the sacrum.

Temperature Control

Additionally and/or alternatively, any of the variations described herein may also incorporate the use of temperature modulation and control to further help prevent the formation of pressure ulcers. For example, the support assembly pad may be controlled to have a temperature which is lower than body temperature to help prevent the formation of pressure ulcers while having an assembly pad controlled to have a temperature which is higher than body temperature can be used to treat pressure ulcers which have already formed upon the body. For example, the assembly pad can be configured to control the contacted skin/tissue temperature to within ±10° C. of body temperature.

Figure 10:
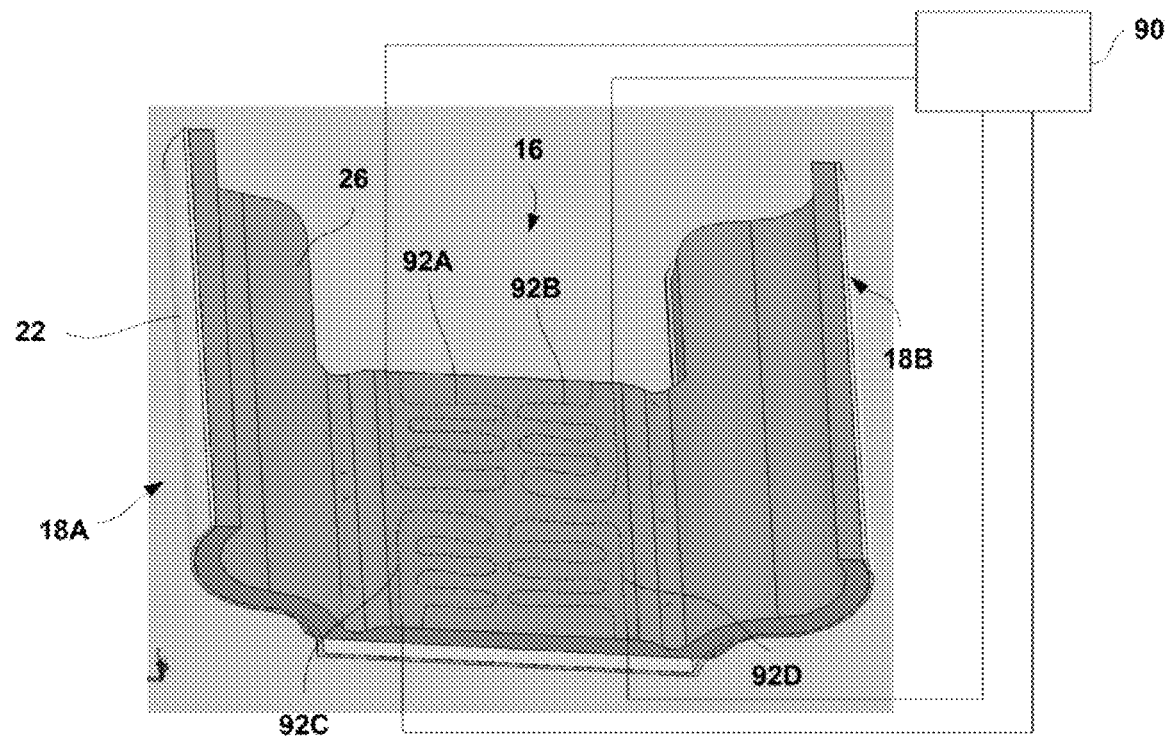
FIG. 10 shows a perspective view of another variation of the support pad assembly having one or more temperature control regions.
Figure 11:
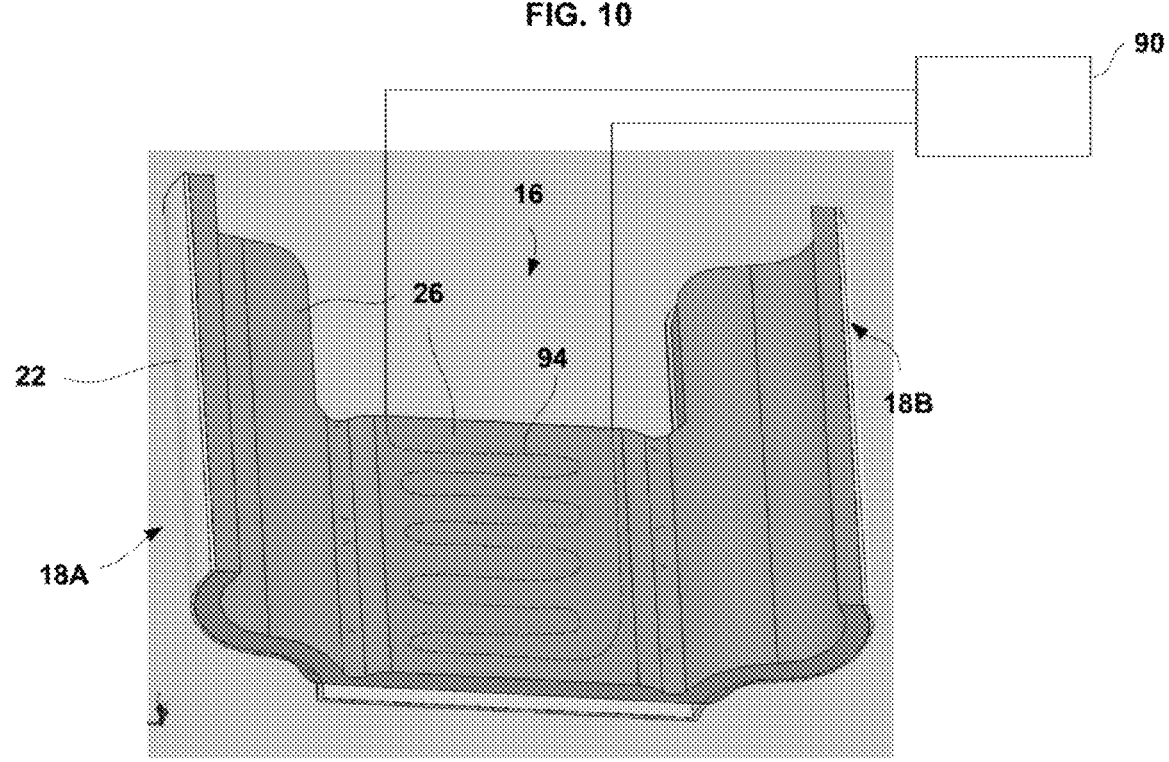
FIG. 11 shows a perspective view of another variation of the support pad assembly having a single temperature control region.

In addition to unidirectional temperature control (either heating or cooling) bidirectional temperature control can be achieved (selectively or alternatively heating and/or cooling). This allows the same assembly pad to be used for prevention and treatment of pressure ulcers. Temperature control can be achieved using any of several various methods and mechanisms. One example is shown in the perspective view of FIG. 10 which illustrates an assembly pad having several individual temperature regions 92A, 92B, 92C, 92D which may be controlled individually or simultaneously to heat or cool specified regions of the pad assembly. Each of the temperature regions may be in electrical communication with a controller 90, e.g., processor, which may be integrated with the pad assembly or arranged as a separate mechanism. FIG. 11 shows another variation where single temperature region 94 may be integrated over the pad assembly to heat or cool the entire pad assembly in contact with the patient.

The unidirectional or bidirectional temperature control may utilize any number of temperature altering mechanisms. For example, thermoelectric cooling and heating elements (e.g., Peltier junctions) may be used or resistive heating and cooling elements may be used. Alternatively, inductive heating and cooling elements may also be used. Additionally and/or alternatively, chemically cooling and/or heating reacting materials (e.g., exothermic and/or endothermic) may be used as the fluid filling the one or more pods and/or pads. In yet another alternative, a cooling or heating fluid may be pumped in a circulating manner with an externally located cooling and/or heating mechanisms in fluid communication with a pumping mechanism.

Figure 12:
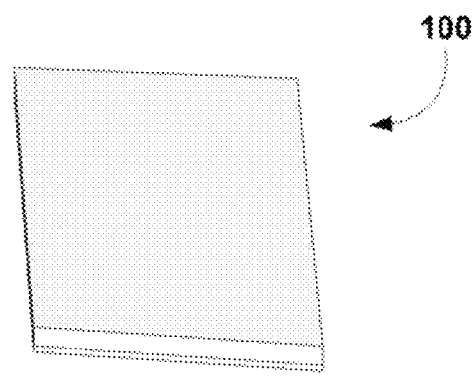
FIG. 12 shows a perspective view of another variation of a support pad configured for alternative uses such as with a wheelchair.
Figure 13:
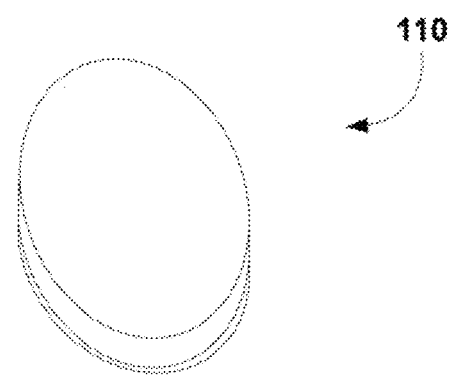
FIG. 13 shows a perspective view of yet another variation of a support pad configured for other regions of the body such as an elbow.

In yet other variations, the pad assembly may be designed for alternative uses. For example, the pad may be configured for use by a patient sitting in a wheelchair, standard chair, or other sitting, standing or sleeping devices or platforms. An example of a simplified pad assembly 100 is shown in the perspective view of FIG. 12. Alternatively, a pad assembly 110 shown in FIG. 13 may be configured for resting, e.g., during surgery, beneath an extremity such as an elbow or any other portion of the body which may come into contact against a hard surface for an extended period of time. The configured pad 110 may cushion, e.g., the ulnar nerve and may include a flat pad with a single fluid pod, for instance.

The applications of the devices and methods discussed above are not limited to particular regions of the body such as the sacrum, trochanter, heel, etc. but may include any number of further applications. Modification of the above-described device and methods for carrying out the invention, and variations of aspects of the invention that are obvious to those of skill in the art are intended to be within the scope of the claims.

What is claimed is:

1. A support assembly, comprising:
    an outer support which is sufficiently flexible to be placed upon a portion of a subject's body;
    one or more spring assemblies positioned adjacent to one another upon an inner surface of the outer support; and,
    a fluid filled outer pad positioned upon the one or more spring assemblies and the inner surface of the outer support such that side portions of the outer pad away from the one or more spring assemblies are adjustably positionable against the subject's body and the outer support is maintained at a distance from the subject's body.

2. The assembly of claim 1 wherein the one or more spring assemblies each comprise one or more biasing elements compressible between the outer support and outer pad.

3. The assembly of claim 2 wherein the spring assemblies each comprise a base and a top layer between which the one or more biasing elements are attached.

4. The assembly of claim further comprising one or more temperature controlled regions within the support assembly.

5. The assembly of claim 4 wherein the one or more temperature controlled regions are configured to increase and/or decrease in temperature relative to a temperature of subject's body.

6. The assembly of claim 1 further comprising an inner pad enclosing the one or more spring assemblies.

7. The assembly of claim 1 wherein the support assembly is configured to be worn in proximity to a sacrum.

8. The assembly of claim 1 further comprising an outer covering over the outer pad which defines one or more openings through the outer covering.

9. A support assembly, comprising:
    an outer support positionable beneath a portion of a subject's body;
    one or more spring assemblies positioned adjacent to one another upon a first surface of the outer support;
    an inner pad enclosing the one or more spring assemblies; and,
    a fluid filled outer pad positioned upon the inner pad and the first surface of the outer support such that side portions of the outer pad away from the one or more spring assemblies are adjustably positionable against the subject's body and the outer support is maintained at a distance from the subject's body.

10. The assembly of claim 9 wherein the one or more spring assemblies each comprise one or more biasing elements compressible between the outer support and outer pad.

11. The assembly of claim 10 wherein the spring assemblies each comprise a base and a top layer between which the one or more biasing elements are attached.

12. The assembly of claim 9 further comprising one or more temperature controlled regions within the support assembly.

13. The assembly of claim 12 wherein the one or more temperature controlled regions are configured to increase and/or decrease in temperature relative to a temperature of subject's body.

14. The assembly of claim 9 wherein the support assembly is configured to be worn in proximity to a sacrum.

15. The assembly of claim 9 further comprising an outer covering over the outer pad which defines one or more openings through the outer covering.

16. A method of supporting a region of a body, comprising:
    positioning a portable support assembly having a flexible outer support in proximity to the region of the body to be supported;
    controlling displacement of one or more spring assemblies positioned along the support assembly beneath the region of the body; and
    redistributing a pressure load from the one or more spring assemblies to a fluid filled outer pad positioned along the support assembly and upon the one or more spring assemblies such that side portions of the outer pad away from the one or more spring assemblies are adjustably positionable against the body and where the outer support is maintained at a distance from the body,
    wherein the redistributed pressure load is exerted upon the body surrounding the supported region.

17. The method of claim 16 wherein positioning comprises wrapping the portable support assembly upon the region of the body via the flexible outer support.

18. The method of claim 16 wherein controlling displacement comprises constraining compression of the one or more spring assemblies via an inner pad enclosing the one or more spring assemblies while further supporting the region of the body via the inner pad.

19. The method of claim 16 wherein redistributing comprises transferring the pressure load from the inner pad to the outer pad via pressure transmission through fluid contained within the inner pad.

20. The method of claim 16 further comprising constraining compression of the one or more spring assemblies via an outer support.

21. The method of claim 16 further comprising controlling a temperature of one or more regions of the body via the support assembly.

* * * * *